United States Patent
Obeid et al.

(10) Patent No.: US 9,668,970 B2
(45) Date of Patent: Jun. 6, 2017

(54) FILM DOSAGE FORM WITH EXTENDED RELEASE MUCOADHESIVE PARTICLES

(71) Applicant: IntelGenx Corp., St.-Laurent (Quebec) (CA)

(72) Inventors: Rodolphe Obeid, Saint-Laurent (CA); Nadine Paiement, Saint-Laurent (CA)

(73) Assignee: IntelGenx Corp., St-Laurent (Quebec) (CA)

( * ) Notice: Subject to any disclaimer, the term of this patent is extended or adjusted under 35 U.S.C. 154(b) by 0 days.

(21) Appl. No.: 14/554,332

(22) Filed: Nov. 26, 2014

(65) Prior Publication Data

US 2015/0150786 A1    Jun. 4, 2015

Related U.S. Application Data

(60) Provisional application No. 61/910,604, filed on Dec. 2, 2013.

(51) Int. Cl.
| | |
|---|---|
| *A61K 47/32* | (2006.01) |
| *A61K 9/00* | (2006.01) |
| *A61K 31/09* | (2006.01) |
| *A61K 31/155* | (2006.01) |

(52) U.S. Cl.
CPC .............. *A61K 9/006* (2013.01); *A61K 31/09* (2013.01); *A61K 31/155* (2013.01); *A61K 47/32* (2013.01)

(58) Field of Classification Search
CPC .................................................... A61K 9/006
See application file for complete search history.

(56) References Cited

U.S. PATENT DOCUMENTS

| | | | |
|---|---|---|---|
| 5,180,578 A | 1/1993 | Gaffar et al. | |
| 5,334,375 A | 8/1994 | Nabi et al. | |
| 5,538,715 A | 7/1996 | Gaffar et al. | |
| 5,690,911 A | 11/1997 | Mirajkar et al. | |
| 6,596,298 B2 | 7/2003 | Leung et al. | |
| 6,923,981 B2 | 8/2005 | Leung et al. | |
| 7,025,983 B2 | 4/2006 | Leung et al. | |
| 7,407,669 B2 | 8/2008 | Leung et al. | |
| 7,867,509 B2 | 1/2011 | Leung et al. | |
| 8,137,713 B2 | 3/2012 | Boyd et al. | |
| 8,491,945 B2 | 7/2013 | Boyd et al. | |
| 2002/0132008 A1* | 9/2002 | Mumper ................ | A61K 9/006 424/487 |
| 2002/0137728 A1* | 9/2002 | Montgomery ................... | 514/99 |
| 2005/0026819 A1* | 2/2005 | Kaniga ............................. | 514/8 |
| 2006/0140883 A1 | 6/2006 | Trivedi et al. | |
| 2007/0224225 A1* | 9/2007 | Irache Garreta et al. . | 424/280.1 |
| 2009/0124535 A1* | 5/2009 | Markland et al. ................. | 514/2 |
| 2011/0293539 A1 | 12/2011 | Ibrahim et al. | |
| 2011/0305768 A1* | 12/2011 | Mao et al. ..................... | 424/499 |
| 2012/0040010 A1 | 2/2012 | Harel et al. | |
| 2012/0087944 A1* | 4/2012 | Tian et al. .................. | 424/209.1 |
| 2012/0121669 A1 | 5/2012 | Fontana et al. | |
| 2012/0121718 A1 | 5/2012 | Lai et al. | |
| 2012/0288548 A1 | 11/2012 | Boyd et al. | |

FOREIGN PATENT DOCUMENTS

WO    WO 2014145699 A1 *    9/2014    ........... A61K 9/0056

OTHER PUBLICATIONS

PR Karn, Z Vanic, I Pepic, N Skalko-Basnet. "Mucoadhesive liposomal delivery systems: the choice of coating material." Drug Development and Industrial Pharmacy, vol. 37(4), 2011, pp. 482-488.*
Z Cui, RJ Mumper. "Bilayer Films for Mucosal (Genetic) Immunization via the Buccal Route in Rabbits." Pharmaceutical Research, vol. 19 No. 7, Jul. 2002, pp. 947-953.*
N Salamat-Miller, M Chittchang, TP Johnston. "The use of mucoadhesive polymers in buccal drug delivery." Advanced Drug Delivery Reviews, vol. 57, 2005, pp. 1666-1691.*
G Yosipovitch, I Kaplan, S Calderon, M David, YH Chan, A Weinberger. "Distribution of Mucosal pH on the Bucca, Tongue, Lips and Palate." Acta Dermatologica Venereologica, vol. 81, 2001, pp. 178-180.*
Jo Morales, JT McConville. "Manufacture and characterization of mucoadhesive buccal films." European Journal of Pharmaceutics and Biopharmaceutics, vol. 77, 2011, pp. 187-199.*
K Yoncheva, E Lizarraga, JM Irache. "Pegylated nanoparticles based on poly(methyl vinyl ether-co-maleic anhydride): preparation and evaluation of their bioadhesive properties." European Journal of Pharmaceutical Sciences, vol. 24, 2005, pp. 411-419.*
Singh, Inderbir et al., "Exploiting the interaction of polymethacrylates with iron oxide for the enhancement of mucoadhesive strength," Pak. J. Pharm. Sci., vol. 27, No. 2., Mar. 2014, pp. 353-350, 8 pages.

(Continued)

*Primary Examiner* — Isaac Shomer
(74) *Attorney, Agent, or Firm* — Butzel Long

(57) ABSTRACT

An orally administered dosage form that facilitates delivery of an agent locally in the buccal cavity for a sustained period of time includes mucoadhesive particles that are made of at least a mucoadhesive material combined with the agent, and which are dispersed in a disintegrating film. The dosage form is capable of delivering an agent to a patient at the desired oral mucosa site over an extended period of time while reducing patient discomfort or annoyance associated with conventional sustained release mucoadhesive films that must reside on the oral mucosa during the period of sustained release.

20 Claims, No Drawings

(56) References Cited

OTHER PUBLICATIONS

Evonik Industries, "Eudragit® polymers—defining targeted drug release," pp. 1-16, 16 pages.
Bernkop-Schnürch, Andreas, Chapter 7 Mucoadhesive Polymers Basics, Strategies, and Future Trends, Polymeric Biomaterials: Structure and Function, vol. 1, CRC Press, 2013, pp. 193-220, 32 pages.

* cited by examiner

FILM DOSAGE FORM WITH EXTENDED RELEASE MUCOADHESIVE PARTICLES

CROSS-REFERENCE TO RELATED APPLICATIONS

This application claims the benefit of U.S. Provisional Application No. 61/910,604, filed Dec. 2, 2013, which is incorporated herein by reference.

FIELD OF THE DISCLOSURE

This disclosure relates generally to controlled release oral dosage forms, especially those oral dosage forms releasing an active agent for local delivery in the buccal cavity.

BACKGROUND OF THE DISCLOSURE

Film dosage forms that provide extended release of an active agent have been known. Such film dosage forms are known to comprise at least two layers, which include at least one mucoadhesive layer to facilitate adhesion of the dosage form to mucosa for an extended period, and a layer that acts as a diffusion barrier that prevents or restricts loss of the active agent from the dosage form to saliva in the oral cavity and ultimately to the gastrointestinal tract. The active agent can be located in the mucoadhesive layer or in a third, reservoir layer between the mucoadhesive layer and the diffusion barrier layer. Such multiple layer film dosage forms require preparation of multiple formulations, casting of multiple film layers, and combining the multiple layers into a composite, such as by casting one layer on another layer, or using a lamination process. As a result, multiple layer film dosage forms for achieving sustained release of an active agent for local delivery in the buccal cavity can be difficult and expensive to produce. Multiple-layer, sustained-release film oral dosage forms can also be annoying to some patients, as the film dosage form must be retained in the oral cavity for an extended period, all the while providing a palpable sensation that many patients find undesirable.

It has been suggested that mucoadhesive particles can be incorporated into oral dosage forms such as capsules, cachets, pills, tablets, lozenges, powders, granules, syrups or liquid suspensions to facilitate transport of an active agent across mucosal barriers.

It has also been suggested that mucoadhesive particles can be incorporated into ophthalmic suspensions or administered rectally, parenterally, intracisternally, intravaginally, intranasally, intraperitoneally, topically, buccally or in an oral or nasal spray.

SUMMARY OF THE DISCLOSURE

The disclosed dosage forms facilitate controlled (e.g., sustained) release of an active agent for local delivery in the buccal cavity, and transport through oral mucosa, while avoiding the discomfort associated with long lasting mucoadhesive films or tablets that must typically reside on the oral mucosa during the period of controlled release. Controlled release of an active agent for local action in the buccal cavity in accordance with the disclosed dosage form is achieved by providing a dosage form in which mucoadhesive particles of a small size (e.g., from several nanometers to several micrometers), which contain the active agent, are dispersed in a disintegrating film. Upon administration in the oral cavity, the film disintegrates (e.g., within an acceptable period of time) and releases the mucoadhesive particles, some of which will contact the oral mucosa and immediately become tenaciously bound to the mucosa. The active agent can be released from the mucoadhesive particles over a prolonged period of time as the mucoadhesive material slowly dissolves or erodes.

In certain disclosed embodiments, the mucoadhesive particles are comprised of a mucoadhesive, non-biodegradable polymer such as polyacrylic acid or a copolymer of maleic anhydride and a methylvinyl ether, maleic acid and a methylvinyl ether or polymethacrylates-based copolymers.

In certain disclosed embodiments, the mucoadhesive particles are comprised of a mucoadhesive biodegradable polymer such as poly-(D,L-lactide-co-glycolide).

The disclosed dosage forms include those having a single layer comprising the active agent-containing mucoadhesive particles dispersed in a disintegrating film.

The disclosed dosage forms can comprise at least two layers, including at least one layer formed from mucoadhesive particles dispersed in a distinguishing film and at least one layer formed from a mucoadhesive, non-mucoadhesive or controlled release composition.

The disclosed dosage forms may comprise a single active agent that is present in only the mucoadhesive particles or in both the mucoadhesive particles and in any of a free form dispersed in the disintegrating film, in a granular, enterically coated, or other controlled release form that is dispersed in the disintegrating film along with the mucoadhesive particles or that is dispersed in a different film of a multiple layer dosage form.

These and other features, advantages and objects of the various embodiments will be better understood with reference to the following specification and claims.

DETAILED DESCRIPTION OF THE DISCLOSED EMBODIMENTS

The disclosed orally administrable dosage forms can be used to provide sustained release of an agent that is delivered for local action in the buccal cavity or under the tongue. The dosage forms can be employed in a variety of treatments in which release of a particular active agent in the buccal cavity or under the tongue over a prolonged period of time provides a beneficial effect. Examples include treatment of gingivitis, buccal ulcers, canker sores, Sjögren's syndrome, oral mucositis, and Behçet's disease.

Sustained release delivery of an agent for local delivery in the buccal cavity is achieved with a dosage form that is essentially imperceptible to the patient. Rather than leaving a mucoadhesive film or patch of substantial size on the oral mucosa during the duration of the extended treatment, the active agent is released from mucoadhesive particles that are adhered to oral mucosa and are of a size that is essentially unnoticeable to the patient. The term "particle" refers to a nanoscopic (1 to 1000 nm) or microscopic (1 to 1000 micrometers) solid or semi-solid aggregate structures. The particles can be spherical or non-spherical (e.g., ellipsoidal or rod-like) structures, with hollow or solid core, such as solid spheres, micelles, vesicles, liposomes or lamellaes. For example, it is possible to employ known techniques to form mucoadhesive particles comprising a mucoadhesive material and an active agent that have a particle size range from a few nanometers (e.g., 5 nm, 10 nm, 50 nm, 100 nm) to a few micrometers (e.g., 1 µm, 100 µm, 200 µm, 300 µm, 500 µm).

In order to facilitate rapid administration and adhesion between the mucoadhesive particles and oral mucosa (e.g., buccal mucosa), the mucoadhesive particles are distributed in a disintegrating film. In certain embodiments, the film disintegrates completely without leaving a noticeable residue. As the film disintegrates, the mucoadhesive particles are released, with those contacting oral mucosa immediately and tenaciously bonding to the mucosa.

In the case where particular areas of the buccal mucosa are targeted for treatment, the dosage form can be placed immediately adjacent or in contact with the affected mucosa. For example, a dosage form used to treat a canker sore on buccal mucosa can be positioned directly on the sore to promote disintegration of the film and adhesion of the residual mucoadhesive particles.

The term "disintegrating" and variations thereof generally refers to the ability of the film dosage forms to break up into particles or completely dissolve within an acceptable period of time (e.g., within less than 5 minutes, within 4 minutes, within 3 minutes, within 2 minutes, or within 1 minute or within 30 seconds of being administered, i.e., placed in the oral cavity of a subject).

Disintegrating films suitable for use in preparing the disclosed dosage forms are typically comprised of at least one water soluble polymer. In certain embodiments, the disintegrating film does not include insoluble polymers or other materials that can leave a gritty, unpleasant residue. Surfactants, polyalcohols, and or plasticizers may be incorporated into the disintegrating film to facilitate or enhance wettability and disintegration of the film.

Water soluble polymers that can be employed in the disclosed films include water soluble cellulose derivatives, including hydroxypropylmethyl cellulose, hydroxyethyl cellulose, hydroxypropyl cellulose; polyvinyl pyrrolidone (PVP); copovidone (a copolymer of 1-vinyl-2-pyrrolidone and vinyl acetate); other copolymers of vinyl pyrrolidone; other polymers or copolymers of substituted vinyl pyrrolidone; derivatives of polyvinyl pyrrolidone; polyethylene oxide, carboxymethyl cellulose; polyvinyl alcohol; natural gums, including xanthan, tragacanth, guar, acacia and arabic gums; and water soluble polyacrylates. Combinations of these water soluble polymers or other water soluble polymers can also be used. Examples of substituted vinyl pyrrolidones include N-vinyl-3-methyl-2-pyrrolidone, N-vinyl-4-methyl-2-pyrrolidone, N-vinyl-5-methyl-2-pyrrolidone, N-vinyl-5,5-dimethyl-2-pyrrolidone, N-vinyl-3,3,5-trimethyl-2-pyrrolidone and others. Examples of monomers that can be copolymerized with vinyl pyrrolidone or substituted vinyl pyrrolidones include vinyl aromatic monomers such as styrene, and acrylate or methacrylate monomers such as methyl methacrylate and 2-dimethylaminoethyl methacrylate.

The terms "surfactant" and "polyalcohol" are intended to have their ordinary meanings. Specifically, the term "surfactant" is intended to mean an amphophilic compound that lowers the surface tension of a liquid, the interfacial tension between two liquids, or the interfacial tension between a liquid and a solid. Examples of surfactants that can be used in a disintegrating film of an oral dosage form are known and include polyoxy-ethylene sorbitan fatty acid esters, an α-hydro-co-hydroxypoly (oxyethylene) poly (oxypropylene) poly(oxyethylene) block copolymer, a polyoxyethylene allyl ether, a polyoxyethylene or a castor oil derivative. Combinations of surfactants can be used. The term "polyalcohol" means a sugar alcohol, which is a hydrogenated form of a carbohydrate having a carbonyl group that has been reduced to a primary or secondary hydroxyl group. Polyalcohols are also distinguishable based on their chemical formula. Polyalcohols have the general formula $H(HCHO)_{n+1}H$, whereas sugars have the general formula $H(HCHO)_n HCO$. Common examples of polyalcohols or sugar alcohols that can be used from the disclosed films include glycol, glycerol, erythritol, threitol, arabitol, xylitol, ribitol, mannitol, sorbitol, galactitol, fucitol, iditol, inositol, volemitol, isomalt, maltitol, lactitol, maltotritol and maltotetraitol.

In certain embodiments, the disclosed films may include a plasticizer. The term "plasticizer" refers to a component that reduces the glass-transition temperature of the film forming polymers (e.g., the water soluble polymer or water soluble polymers in the film). The plasticizer increases the flexibility, enhances elasticity and reduces brittleness of the film. Examples of plasticizers that can be used in the disclosed film oral dosage forms include polyethylene glycol, triacetin, triethyl citrate, tributyl citrate, acetyl tributyl citrate, acetyl triethyl citrate, trioctyl citrate, acetyl trioctyl citrate, trihexyl citrate, dibutyl sebacate, etc. Plasticizer may be added in an amount up to 25% of the total mass of the film oral dosage form, such as from 0.5% to 25%, 1% to 20%, 2% to 15% or 5% to 10%.

Optionally, an agent can be incorporated into the disintegrating film in an immediate release form (i.e., a form that is not incorporated into sustained release mucoadhesive particles), such as in a free particulate form or immediate release granular form. The agent incorporated into the disintegrating film in an immediate release form can be the same agent as in the mucoadhesive particles or a different agent.

The term "agent" refers to any agent that is being administered orally to a subject and includes pharmaceutically active agents, nutraceutically active agents, flavoring agents, and breath freshening agents. Examples of pharmaceutically active agents include ACE-inhibitors, antianginal drugs, anti-arrhythmics, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-fungal agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, tadalafil, and vardenafil, fertility agents, gastrointestinal agents, homeopathic remedies, hormones, hypercalcemia and hypocalcemia management agents, immunomodulators, immunosuppressives, anti-migraine preparations such as rizatriptan, eletriptan and zolmitriptan, motion sickness treatments, muscle relaxants, obesity management agents, osteoporosis preparations, oxytocics, parasympatholytics, parasympathomimetics, prostaglandins, psychotherapeutic agents, respiratory agents, sedatives such as lorazepam or diazepam, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents such as alprazolam, anti-ulcer agents, anti-inflammatory substances, coronary dilators, cerebral dilators, peripheral vasodilators, psycho-tropics, stimulants, anti-hypertensive drugs, vasoconstrictors, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-astmatics, cough suppressants, mucolytics, DNA and genetic modifying drugs, and combinations thereof. Examples of nutraceutically active agents include various dietary supplements, vitamins, minerals, herbs and nutrients. Breath freshening agents include, for example, spearmint oil, cinnamon oil, peppermint oil, clove oil, menthol, etc.

The total amount of agent(s) that can be incorporated in the disintegrating films disclosed herein is generally from 0.01% to 80% by total weight of the film, such as 1% to 60%, 2% to 50%, or 5% to 40% by total weight of the film.

Examples of mucoadhesive materials that can be used to prepare the mucoadhesive particles include poly(ethylene oxide), polyvinyl pyrrolidone, poly(acrylic acid) derivatives (e.g., commercially available Carbopol®), polycarbophil, polyoxyalkylene ethers, polymethacrylates, polymethacrylates-based copolymers (e.g., commercially available Eudragit®), biodegradable polymers such as poly(D,L-lactide-co-glycolide) (e.g., commercially available Resomer®), anionic biopolymers such as hyaluronic acid, or sodium carboxymethylcellulose, cationic biopolymers such as chitosan or poly(L-lysine) and other cellulose derivatives. Other mucoadhesive polymers that can be used include methyl vinyl ether-maleic acid, a mixed salt of sodium/calcium methyl vinyl ether-maleic acid, methyl vinyl ether-maleic anhydride, and half esters (monoethyl; monobutyl and isopropyl ester) of methyl vinyl ether-maleic anhydride copolymers (e.g., commercially available Gantrez®).

The agent incorporated into the mucoadhesive particles can be any of the previously listed active agents that can optionally be added, along with the mucoadhesive particles, to the disintegrating film in immediate release form or in a controlled release form that is not incorporated into a mucoadhesive.

Examples of agents that can be beneficially employed in the mucoadhesive particles are those for treating fungal or bacterial infections, gingivitis, buccal ulcers, canker sores, Sjögren's syndrome, oral mucositis, Behçet's disease or other conditions that can be beneficially treated from long exposure or controlled release (e.g., sustained release) of an agent for local delivery in the buccal cavity. Systemic treatments where there is a pronounced food effect or the bioavailability of the active product or for active products that need to be absorbed in the upper gastrointestinal tract could also benefit from use of the disclosed dosage forms.

Particular categories of agents that can be incorporated into the mucoadhesive particles include antimicrobial agents including antibacterial agents and/or antifungal agents, such as triclosan, chlorhexidine, doxycycline, tetracycline, minocycline, neomycin, caspofungin, miconazole, micafungin, and anidulafungin; topical analgesic agents such as benzydamine, amlexanox, lidocaine and diclofenac; corticosteroid anti-inflammation agents such as hydrocortisone, beclomethasone dipropionate, clobetasol, betamethasone sodium phosphate, and dexamethasone; agents for modulating immune response such as prednisolone, colchicines, pentoxifylline, azothioprine, thalidomide, dapsone, mycophenolate, mofetil, adalimunab, vitamin B12, clofazimine, fevamizole, montelukast, and sulodexide; and disease modifying antirheumatic agents, such as methotrexate and hydroxychloroquine. These and other agents can be used alone or in combination, either incorporated into the disintegrating film in an immediate release form or non-mucoadhesive controlled release form, in the mucoadhesive particles, or both.

As a specific example, for the treatment of canker sores, an antimicrobial agent and a topical analgesic agent may be used together in the mucoadhesive particles to provide simultaneous treatment and relief from pain. Alternatively, or in addition, the topical analgesic agent can be incorporated as an immediate release agent in the disintegrating film. As another example, Sjogren's disease can be treated with a combination of cevimeline and/or pilocarpine, and optionally with a corticosteroid anti-inflammatory agent and/or a disease-modifying anti-rheumatic agent, which optional agents can be added in a free form to the film, to the mucoadhesive particles, or both to the mucoadhesive particles and in free form to the film.

In some embodiments, the particles are first formed using precipitation techniques, followed by coating of the particles with a block copolymer. Precipitation techniques (e.g., microprecipitation techniques, nanoprecipitation techniques) may involve forming a first solution comprising the polymeric material (or other hydrophobic material) and a solvent, wherein the polymeric material is substantially soluble in the solvent. The solution may be added to a second solution comprising another solvent in which the polymeric material is substantially insoluble, thereby forming a plurality of particles comprising the polymeric material. In some cases, one or more surfactants, materials, and/or bioactive agents may be present in the first and/or second solution.

In an exemplary embodiment, a method of forming the particles includes using a poly(ethylene glycol)-vitamin E conjugate (hereinafter "PEG-VitE conjugate" or "VP5k"). The PEG-VitE conjugate can act as a surfactant, may aid in stabilizing the particles, and/or may aid in encapsulating the particle material. In some cases, a method for forming a plurality of particles using PEG-VitE comprises forming a solution comprising a polymeric material (or other hydrophobic material), and adding the solution to a solvent in which the polymeric material is substantially insoluble. The PEG-VitE conjugate may be present in the solution comprising the polymeric material and/or the solvent to which the solution is present. Upon addition of the solution comprising the polymeric material to the solvent, a plurality of particles form, which are stabilized by the PEG-VitE conjugate. The PEG-VitE conjugate may be present in the solvent or solution at about 0.1%, 0.5%, 1.0%, 1.5%, 1.65%, 2%, 3%, 4%, 5%, 10%, 20% weight percent, or greater. Examples of solvents that may be suitable for use in the invention include, but are not limited to, acetonitrile, benzene, p-cresol, toluene, xylene, mesitylene, diethyl ether, glycol, petroleum ether, hexane, cyclohexane, pentane, dichloromethane (methylene chloride), chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like.

Another technique that may be used for preparing the mucoadhesive particles is a solvent displacement technique.

Solvent displacement method is based on spontaneous emulsification of an organic internal phase (i.e., acetone, ethanol, or butyl alcohol alone or as a mixture), also referred to as the solvent phase, into an aqueous (mainly water) or hydroalcoholic external phase (alcohol/water mixture).

The solvent phase is a solution of a polymer (i.e., Eudragit® family (polymethacrylates-based copolymers), Resomer® family (such as poly(D,L-lactide-co-glycolide), or Gantrez® family (copolymer of maleic anhydride)) and the active substance (i.e., antifungal, antibacterial, gingival treatments, buccal ulcer treatments, canker sore treatments) in an organic solvent totally miscible with water.

The polymer and the active substance are dissolved in a water-miscible solvent of intermediate polarity, leading to the precipitation of the particles. This phase is injected into a stirred aqueous or hydroalcoholic solution in the presence or absence of a stabilizer as a surfactant. Polymer deposition on the interface between the water and the organic solvent, caused by fast diffusion of the solvent, leads to the instantaneous formation of a colloidal suspension.

However, it is possible to use either two organic phases or two aqueous phases or mixtures thereof as long as solubility, insolubility and miscibility conditions are satisfied. Regarding particle preparation, the organic phase is mixed with the stirred aqueous phase in one shot, stepwise, dropwise or by controlled addition and stirring rate. The organic solvent is removed from the system by using evaporation under reduced pressure. The organic phase could also be kept totally or in portion to prepare the wet blend for the film formulation.

Alternatively, the mucoadhesive particles can be prepared by single or multiple emulsification technique. The organic inner phase is a solution of the polymer in the presence or absence of the active substance in an organic solvent system (e.g., ethyl acetate, isobutyl acetate, methyl ethyl ketone (MEK), dichloromethane (DCM), or ethyl formate alone or in combination) partially miscible or non-miscible with the outer phase (water or silicone oil). The latter phase (outer) can be saturated or not with an organic solvent. It is possible for some active substances to be dissolved first in an aqueous phase and then emulsified in an organic partially miscible solvent system to form the first microemulsion droplet, and then emulsified within the outer phase. The outer phase comprises the dispersion of a stabilizing agent (e.g., polyvinyl alcohol (PVA), polysorbates) or sodium lauryl sulfate prepared by using solvent-saturated phase.

Optionally, a cross-linking agent can be used during the production of the mucoadhesive particles to improve their stability and extend the residence time. Examples of cross-linking agents that may be suitable for use in the invention include, but are not limited to, acetate salts such as magnesium or calcium acetate, carbodiimide and diamine compounds or their derivatives.

For both techniques, the mucoadhesive particles are formed instantaneously with a size range between 100 nm and 100 μm depending on the operating conditions. The study of the operating conditions related to the particle formation can be investigated from different angles to obtain specific particle compositions, morphologies and sizes, and improve the local extended residence time.

The two methods allow active substance loading range between 0.5-20% and entrapment efficiencies range between 50-99.9%.

Production of Antimicrobial Drug Loaded Gantrez AN Mucoadhesive Particles

Solvent displacement method: 20 mg of antimicrobial drug were dissolved in 5 ml of Gantrez AN/organic phase solution at 2% w/v. The mucoadhesive particles were produced by the addition of 20 ml of hydroalcoholic solution (1:1) under stirring for 10 min at 4° C. The alcohol is removed under reduced pressure using a rotavapor. The aqueous suspension of drug loaded Gantrez particles were collected and used next in the formulation of water soluble films.

Emulsification method: 20 mg of antimicrobial drug were dissolved in 5 ml of Gantrez AN/MEK solution at 2% w/v. The organic phase (O) was emulsified in an aqueous/PVA solution (W) using a high speed homogenizer for 5 min. to achieve an O/W emulsion system. If necessary, the organic solvent could be removed by extraction/evaporation or filtration technique. The drug loaded Gantrez particles were collected and used next in the formulation of water soluble films.

The suspended particles are further dissolved with water. Sweetener, flavor and a pore former are added and stirred until a homogeneous dispersion is obtained. Polyethylene oxide is then added gradually to the wet blend and mixed until completely dissolved. The wet blend is then coated on support liner and dried in an oven until the moisture level reaches less than 5%. The obtained product is cut and packaged.

Conventional mixing techniques can be employed for dispersing the mucoadhesive particles and other optional active agents into the film composition, which typically comprises the mucoadhesive polymer dissolved in a suitable solvent, and contains any optional ingredients such as plasticizers, polyalcohols, and surfactants. The film composition containing the mucoadhesive particle and any optional active agents present in either a free, immediate release form, or in a non-mucoadhesive controlled release form can be cast and dried to form a film using known processes.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. An oral dosage form providing transport of an agent for local delivery in a buccal cavity of a subject for a sustained period of time, comprising:
    a disintegrable film; and
    mucoadhesive particles dispersed in the disintegrable film, the particles comprising a mucoadhesive material exhibiting adhesivity to mucosa in the buccal cavity and at least a first active agent, wherein the mucoadhesive material is a copolymer of D,L-lactide and/or glycolide monomers.

2. An oral dosage form providing transport of an agent for local delivery in a buccal cavity of a subject for a sustained period of time, comprising:
    a disintegrable film; and
    mucoadhesive particles dispersed in the disintegrable film, the particles comprising a mucoadhesive material exhibiting adhesivity to mucosa in the buccal cavity and at least a first active agent, wherein the mucoadhesive material is a polymethacrylates-based copolymer.

3. The dosage form of claim 1 or 2, in which the dosage form has a single layer comprising the mucoadhesive particles dispersed in the disintegrable film.

4. The dosage form of claim 1 or 2, in which the dosage form comprises at least two layers including at least one layer formed from mucoadhesive particles dispersed in a film and at least one layer formed from a mucoadhesive, non-mucoadhesive or controlled release composition.

5. The dosage form of claim 4, in which the second layer comprises an active agent that is different from the agent in the first layer.

6. The dosage form of claim 4, in which the second layer comprises a flavor.

7. The dosage form of claim 5, in which the second layer comprises an agent that is the same as the agent in the first layer.

8. The dosage form of claim 1 or 2, in which the mucoadhesive particles comprise a second agent different from the first agent.

9. The dosage form of claim 1 or 2, in which the first agent is an antibacterial agent.

10. The dosage form of claim 1 or 2, in which the first agent is an antifungal agent.

11. The dosage form of claim 1 or 2, in which the first agent is an antigingivitis agent.

12. The dosage form of claim 1 or 2, in which the first agent is triclosan.

13. The dosage form of claim 1 or 2, in which the first agent is chlorhexidine.

14. The dosage form of claim 1 or 2, in which the first agent is a non-steroidal anti-inflammatory topical analgesic.

15. The dosage form of claim 1 or 2, in which the first agent is at least one of the group consisting of benzydamine, amlexanox, lidocaine, diclofenac, caspofungin, micafungin and anidulafungin.

16. The dosage form of claim 5, in which the first agent is an antimicrobial agent and the second agent is an analgesic agent.

17. The dosage form of claim 8, in which the first agent is an antimicrobial agent and the second active agent is a topical analgesic agent.

18. The dosage form of claim 1 or 2, in which the first active agent is at least one of cevimeline and pilocarpine.

19. The dosage form of claim 5, in which the first active agent is at least one of cevimeline and pilocarpine and the second active agent is at least one of a topical analgesic, a corticosteroid anti-inflammatory agent, and a disease-modifying anti-rheumatic agent.

20. The dosage form of claim 8, in which the first active agent is at least one of cevimeline and pilocarpine and the second active agent is at least one of a topical analgesic, a corticosteroid anti-inflammatory agent, and a disease-modifying anti-rheumatic agent.

* * * * *